US00PP09517P

United States Patent [19]

Schrama

[11] Patent Number: Plant 9,517

[45] Date of Patent: Apr. 23, 1996

[54] CARNATION PLANT NAMED FRANS HALS

[75] Inventor: Ronald Schrama, Vinkeveen, Netherlands

[73] Assignee: M. Lek & Zonen B.V., Nieuwveen, Netherlands

[21] Appl. No.: 393,372

[22] Filed: Feb. 23, 1995

[51] Int. Cl.[6] ..... A01H 5/00

[52] U.S. Cl. ..... Plt./70.7

[58] Field of Search ..... Plt./70.7

*Primary Examiner*—James R. Feyrer

*Attorney, Agent, or Firm*—Foley & Lardner

[57] ABSTRACT

A new and distinct cultivar of carnation plant named Frans Hals, characterized by its bright red-purple base flower color, with darker red striations or speckles, generally flat flower form, generally wavy petal form, with crenate-dentate outer margin; relatively long and narrow leaves which are blue-green in color, and its funnel-shaped calyx with short, acute lobes infused with anthocyanin.

2 Drawing Sheets

The present invention comprises a new and distinct cultivar of Carnation, botanically known as *Dianthus caryophyllus* L., and referred to by the cultivar name Frans Hals.

Frans Hals is the product of a planned breeding program carried out in Nieuwveen, The Netherlands.

Frans Hals was originated by the inventor from a hybridization made in Nieuwveen in 1985. The female parent was the cultivar identified as Pico. The male parent was the cultivar identified as ML 014002.

Frans Hals was discovered and selected as one flowering plant within the progeny of the stated parentage by the inventor in a controlled environment in Nieuwveen.

The first act of asexual reproduction of Frans Hals was accomplished when vegetative cuttigns were taken from the initial selection in July 1986 in a controlled environment in Nieuwveen by or under the supervision of the inventor.

Horticultural examination of selected units initiated following asexual reproduction has demonstrated that the combination of characteristics as herein disclosed for Frans Hals are firmly fixed and are retained through successive generations of asexual reproduction.

Frans Hals has not been observed under all possible environmental conditions. The phenotype may vary somewhat with variations in environment such as temperature, light intensity and daylength, without, however, any variation in genotype.

The following observations, measurements and comparisons describe plants grown in Wageningen and Nieuwveen, The Netherlands under greenhouse conditions which closely approximate those generally used in commercial practice.

The following traits have been repeatedly observed and are determined to be basic characteristics of Frans Hals which in combination distinguish this carnation as a new and distinct cultivar:

1. The base color of the flowers is a bright red-purple striated or speckled with a secondary dark red color.

2. The top surface of the fully opened corolla is generally flat, merging into convex sides.

3. Foliage is typical for carnations, relatively long and narrow, and blue-green in color.

4. Individual flower petals are generally wavey with the outer margin being crenate-dentate.

5. The calyx is funnel shaped, with the lobes being short and acute in shape and infused with anthocyanin.

The accompanying color photographic drawings show typical inflorescence and foliage characteristics of Frans Hals.

The photo on sheet 1 illustrates a potted plant of the new cultivar with many open flowers and buds.

The photo on sheet 2 shows various plant parts, including flowers, individual petals, stems and calyx. Colors are as nearly true as possible with illustration of this type, although the true base color of the flowers (67A) is not precisely shown in either of the photographs.

In the following description, color references are made to The Royal Horticultural Colour Chart. Color values were determined indoors in a north light in Wageningen.

Classification:

*Botanical.*—*Dianthus caryophyllus* L., cv. Frans Hals.

*Commercial.*—Pot carnation.

INFLORESCENCE CHARACTERISTICS

Flowering response: 12–20 weeks after planting rooted cuttings and with one pinch.

Number of buds and flowers per stem: 1–5.

Peduncle length: 18–22 cm.

Flower:

*Size.*—Approximately 2.5 cm.

*Type.*—Double.

*Form.*—Top surface flat, periphery of flower convex.

*Buds.*—Cylindrical in shape just before opening.

*Calyx.*—Funnel-shaped; lobes are short and acute in shape, and convex, and infused with anthocyanin; apex of both outer and inner lobes of epicalyx is acute.

*Petals.*—Generally wavy in cross-section, margin is crenate-dentate; see photo for petal shape and size.

Color:

*General tonality from a distance of three meters.*—Dark red.

*Upper surface.*—Main color (claw excluded) is red-purple 67A, with dark red striations or speckles clearly visible; color fades very little during maturation.

Fragrance: Medium.

Reproductive organs:

*Androecium.*—Present.

*Gynoecium.*—Ovaries are obovoid in shape, mainly green in color, with surface being ribbed; no transformation of ovaries into flower buds; generally 3 styles but occasionally 4; styles do not have a shoulder; color of stigma is purple.

PLANT CHARACTERISTICS:

Growth habit: Vigorous growth habit.

Branching Pattern: 2–5 side branches per stem.

Height: Approximately 25 cm in height at time of flowering.

Stems: Straight and rigid, firmly supporting flowers.

Foliage:

*Shape.*—Obovate; upper surface concave in cross-section; longitudinal axis recurved.

*Texture.*—Glancosity is present, margin ciliated.

*Size.*—Length approximately 5.0–7.0 cm; width approximately 0.5 cm.

*Color.*—Typical carnation, blue-green.

It is claimed:

1. A new and distinct cultivar of carnation plant named Frans Hals, as illustrated and described.

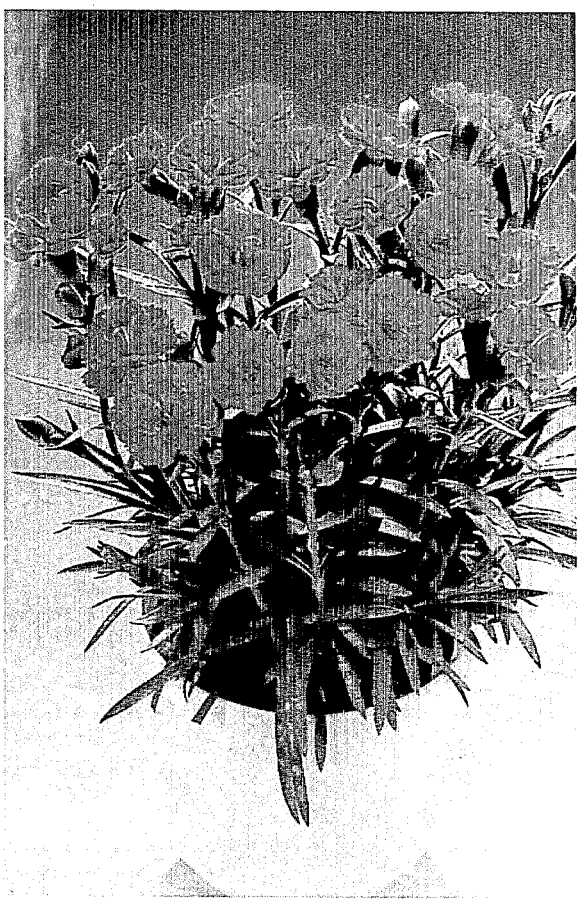

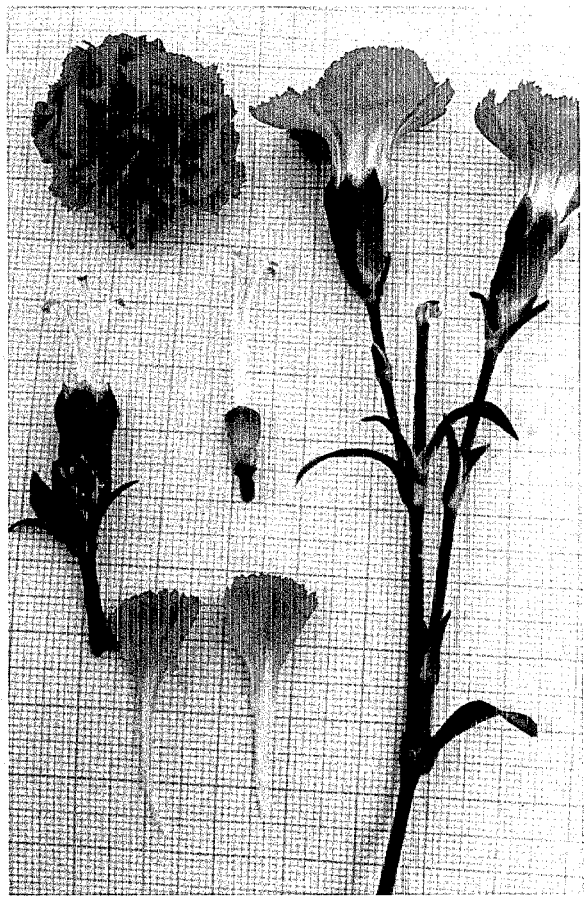

* * * * *